United States Patent [19]

Kolb et al.

[11] Patent Number: 4,707,498

[45] Date of Patent: Nov. 17, 1987

[54] FLUORINATED DIAMINOALKYNE DERIVATIVES

[75] Inventors: Michael Kolb, Truchtersheim; David A. Kendrick, Illkirch Graffenstaden, both of France

[73] Assignee: Merrell Dow Pharmaceuticals Inc., Cincinnati, Ohio

[21] Appl. No.: 818,848

[22] Filed: Jan. 14, 1986

[51] Int. Cl.⁴ .................. C07C 87/24; C07C 87/22; A61K 31/13
[52] U.S. Cl. ............................ 514/671; 564/509; 564/510
[58] Field of Search ................ 564/509, 510; 514/671

[56] References Cited

U.S. PATENT DOCUMENTS 4,139,563  2/1979  Metcalf et al. ............... 564/509
4,421,768  12/1983  Casara et al. ............... 564/509

Primary Examiner—Charles F. Warren
Assistant Examiner—John A. Sopp
Attorney, Agent, or Firm—Stephen L. Nesbitt

[57] ABSTRACT

Novel fluorinated diaminoalkyne derivatives are inhibitors of ornithine decarboxylase enzyme and have the following general Formula I:

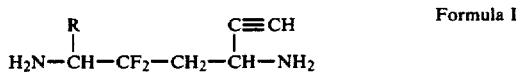

wherein R represents $C_1$–$C_4$ alkyl, or preferably, hydrogen.

10 Claims, No Drawings

FLUORINATED DIAMINOALKYNE DERIVATIVES

FIELD OF THE INVENTION

The invention relates to novel pharmaceutically useful fluorinated diaminoalkyne derivatives and pharmaceutically acceptable salts thereof which are inhibitors of a decarboxylase enzyme (ornithine decarboxylase) involved in polyamine formation in organisms. The invention provides the compounds per se, pharmaceutical compositions comprising said compounds, methods of medical treatment using said compounds and processes for preparing said compounds.

BACKGROUND OF THE INVENTION

The decarboxylation of ornithine to putrescine, a reaction catalyzed by the enzyme ornithine decarboxylase (ODC), is the first step in the biosynthesis of the polyamines spermidine and spermine. Spermidine is formed by the transfer of an activated aminopropyl moiety from S-adenosyl S-methyl homocysteamine to putrescine, while spermine is formed by the transfer of a second aminopropyl group to spermidine. S-Adenosyl S-methyl homocysteamine is formed by the decarboxylation of S-adenosylmethionine (SAM), a reaction catalyzed by the enzyme S-adenosylmethionine decarboxylase (SAM-DC).

The polyamines, which are found in animal tissues and microorganisms, are known to play an important role in cell growth and proliferation. The onset of cell growth and proliferation is associated with both a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in embryonic tissue; in the testes, ventral prostrate, and thymus; in tumor tissue; in psoriatic skin lesions; and in other cells undergoing rapid growth or proliferation.

Since putrescine is the precursor of both spermidine and spermine, blockade of the conversion of ornithine to putrescine, such as by inhibition of ODC, should prevent new biosynthesis of these polyamines and, thus, provide beneficial physiological effects.

We have disclosed in U.S. Pat. No. 4,139,563 that inter alia compounds of the following Formula A are inhibitors of ornithine decarboxylase:

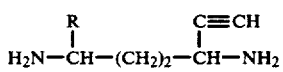

Formula A wherein R represents hydrogen or $C_1$–$C_4$ alkyl.

Further, we have disclosed in U.S. Pat. No. 4,421,768 that compounds of the following Formula B also are ornithine decarboxylase inhibitors:

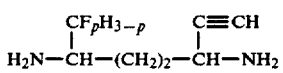

Formula B wherein p represents 1 or 2.

SUMMARY OF THE INVENTION

The compounds of the present invention are represented by the following general Formula I:

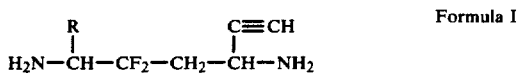

Formula I wherein R represents hydrogen or $C_1$–$C_4$ alkyl.

Pharmaceutically acceptable salts of the compounds of general Formula I are also within the scope of the invention.

The compounds of Formula I inhibit ornithine decarboxylase enzyme (ODC) in vitro and in vivo, and produce a decrease in putrescine and spermidine concentrations in cells in which active biosynthesis of polyamines is taking place. The compounds of Formula I, therefore, are useful in mammals for controlling undesirable cell growth or proliferation. The compounds of Formula I are useful pharmacological agents for treating those diseases or conditions that are known in the art to be characterized by high ODC activity. In particular, the compounds are useful systemically for controlling the growth of tumor tissues in mammals, for treating benign prostatic hypertrophy and for controlling the growth of pathogenic parasitic protozoa in infected domestic animals and humans.

The compounds of Formula I can also be employed to study the presence and physiological function of ODC inhibition in biological systems and its relationship to pathological processes.

It will be recognized that the compounds of Formula I can be substituted at an amino group with any group known in the art to be capable of cleavage in vivo (enzymatically or chemically) to generate a free amino group. Compounds which contain such cleavable substituents and which, therefore, can be converted in vivo to a compound of Formula I will be equivalent to the compounds of Formula I for the purposes of this invention. Such derivatives can be prepared in manner known per se for the compounds of Formula I. A presently preferred derivative is the N-glutamyl derivative.

The ODC activity of the compounds can be determined in vitro by the method described by B. Metcalf et al. *J. Am. Chem. Soc.*, 100, 2551 (1978). The ODC activity of the compounds of Formula I can be determined in vivo by the method of C. Danzin, *Biochemical Pharmacology*, 28, 627 (1979).

DETAILED DESCRIPTION OF THE INVENTION

In general Formula I, R represents hydrogen or $C_1$–$C_4$ alkyl, especially methyl, but preferably R is hydrogen.

References in this Specification, including the claims, to an alkyl group mean a straight or branched chain alkyl group and, in the case of an alkyl group having structural isomers, includes all of those isomers and mixtures thereof unless a particular isomer is specified or clearly implied by the context. Illustrative examples of straight or branched chain alkyl groups having 1 to 4 carbon atoms are methyl, ethyl, n-propyl, iso-propyl and n-butyl.

Illustrative examples of pharmaceutically acceptable salts of the compounds of this invention include nontoxic acid addition salts formed with inorganic acids, such as hydrochloric, hydrobromic, sulfuric and phosphoric acid, or with organic acids, such as, organic carboxylic acids, for example salicylic, maleic, malonic, tartaric, citric and ascorbic acids, and organic sulfonic acids, for example methane sulfonic acid.

Illustrative examples of compounds of the present invention are the following:

1,4-diamino-2,2-difluoro-hex-5-yne;
2,5-diamino-3,3-difluoro-hept-6-yne; and
3,6-diamino-4,4-difluoro-oct-7-yne.

It is believed that the compounds of general Formula I are "substrate-induced irreversible inhibitors" of ornithine decarboxylase. Such inhibitors are also known in the art as "enzyme-activated irreversible inhibitors", "suicide enzyme inhibitors", "$K_{cat}$ inhibitors", or "mechanism-based inhibitors". In order for a compound to be a substrate-induced irreversible enzyme inhibitor, the compound must be a substrate for the target enzyme, and the compound must contain a latent reactive group susceptible of being unmasked as the result of the normal catalytic action of the enzyme. The unmasking of the latent reactive group by the action of the enzyme generates a reactive function which alkylates a nucleophilic residue present at the active site of the enzyme. Thus, there is formed a covalent bond between the inhibitor and the enzyme at the active site resulting in irreversible inactivation of the enzyme. Such inhibitors are extremely specific since the inhibitor must be a substrate for the target enzyme and since biotransformation of the inhibitor by the target enzyme is required before the enzyme is inactivated. Although it is believed that the compounds of general Formula I generally exert their action by means of a substrate-induced mechanism, inhibition may occur by other mechanisms, such as by competitive inhibition.

As used herein, the term "tumor tissue" means both benign and malignant tumors or neoplasms, and includes leukemias, lymphomas, melanomas, and sarcomas. The term "controlling the growth of tumor tissue" as used herein means slowing, interrupting, arresting, or stopping the growth of a rapidly proliferating tumor in a warm blooded animal. It should be understood that the administration of a compound of the Formula I does not provide a "cure" for the tumor in the sense that the tumor tissue is destroyed or totally eliminated from the animal being treated.

For controlling the growth of tumor tissues, a compound of Formula I can be administered to the patient in conjunction with other therapeutic methods or in combination with cytotoxic drugs known in the art to be useful for cancer chemotherapy. For example, a compound of Formula I can be administered in conjunction with surgical excision of the tumor or with radiation therapy, hormonal treatment, immunotherapy, or local heat therapy. Moreover, in a preferred manner, a compound of Formula I can be administered to a patient in combination with a chemical cytotoxic agent known in the art to be useful for tumor chemotherapy. When such combination therapy is employed for the treatment of a tumor, the cancer chemotherapeutic agent may be administered at a dosage known in the art to be effective for treating the tumor. However, a compound of Formula I may produce an additive or synergistic effect with a chemotherapeutic agent against a particular tumor. Thus, when such combination antitumor therapy is used, the dosage of the chemotherapeutic agent administered may be less than that administered when the agent is used alone. In combination with a compound of Formula I, the chemotherapeutic agent may, therefore, be administered at a lower dosage level or at less frequent intervals as compared to the chemotherapeutic agent when used alone.

In combination with a compound of Formula I, any cancer chemotherapeutic agent may be employed. Drugs commonly used for cancer chemotherapy are described in *The Medical Letter*, Vol. 22, No. 24 (Issue 571), Nov. 28, 1980, Published by the Medical Letter, Inc., New Rochalle, N.Y., 10801. Illustrative examples of cytotoxic chemotherapeutic agents are cyclophosphamide, methotrexate, prednisone, 6 mercaptopurine, procarbozine, daunorubicin, vincristine, vindesine, vinblastine, chlorambucil, cytosine arabinoside, 6-thioguanine, thio TEPA, 5-fluorouracil, 5-fluoro-2deoxyuridine, 5-azacytidine, nitrogen mustard, 1,3-bis(2-chloroethyl)-1-nitrosourea (BCNU), 1-(2-chloroethyl)-3-cyclohexyl-1-nitrosourea (CCNU), busulfan, adriamycin, bleomycin, cycloleucine or methylglyoxal bis(-guanylhydrazone) (MGBG). Other cancer chemotherapeutic agents will be apparent to those skilled in the art.

The effect of the compounds of Formula I for the control of the growth rate of rapidly proliferating tumor tissue can be assessed in standard animal tumor models after oral or parenteral administration. For example, the antitumor effects can be demonstrated in the following models: (a) L1210 leukemia in mice, (b) EMT 6 tumor in Balb/C mice, (c) 7,12-dimethylbenzanthracene-induced (DMBA-induced) mammary tumor in rats, or (d) Morris 7288 C or 5123 hepatoma in Buffalo rats. In addition, the antitumor effects of the compounds in combination with chemotherapeutic agents can be demonstrated in animal models.

When, in the treatment of a malignant neoplastic disease, a compound of Formula I is administered in combination with a chemotherapeutic agent, the therapeutic effect of the chemotherapeutic agent may be potentiated in that the remission produced by the chemotherapeutic agent may be enhanced and regrowth of the tumor tissue may be slowed or prevented. Use of such combination therapy therefor allows smaller doses or fewer individual doses of the chemotherapeutic agent to be employed. Thus, the detrimental and/or debilitating side effects of the chemotherapeutic agent are minimized while, at the same time, the antitumor effects are enhanced. The term "combination therapy" contemplates the administration of a compound of Formula I immediately prior to the beginning of chemotherapy, concomitantly with chemotherapy, or during the period of time immediately following cessation or discontinuance of chemotherapy.

When chemotherapy results in remission of the tumor and all tumor cells are not destroyed, regrowth of the tumor may be prevented or slowed indefinitely by continued treatment with a compound of Formula I. Thus, a compound of Formula I can be administered to stop or slow the growth of the tumor during the periods when chemotherapy using a cytotoxic agent may be temporarly discontinued.

A preferred cytotoxic agent for combination therapy with a compound of Formula I is methylglyoxal bis(-guanylhydrazone), herein referred to as MGBG, which is also an inhibitor of S-adenosyl methionine decarboxylase. The activity of MGBG as a chemotherapeutic agent in the treatment of neoplastic diseases is well documented. For example, W. A. Knight et al. *Cancer Treat. Rep.*, 43, 1933, (1979) have reported that a dose of MGBG administered intravenously once or twice week to patients in the advanced stages of carcinoma of the bladder, esophagus, lung, pancreas, colon, kidney, breast and prostate, oat cell carcinoma, adenocarcinoma, lymphoma, hepatoma, melanoma, leukemia, or Edwing's sarcoma produced measurable regression of the tumor in many of the patients treated and complete disappearance of the disease in two of the 65 treated patients.

The amount of MGBG to be administered may be the same as the amount known in the art to be effective for tumor therapy. Effective and non-toxic dosages are determined by the physician in each case, taking into account the condition of the individual patient. For example, a dosage of 250–500 mg per meter$^2$ of body surface area may be infused once or twice weekly in 100 ml of aqueous 5% dextrose solution over a 30 min period. Combination therapy with a compound of Formula I improves the response of the tumor tissue to the cytotoxic effect of MGBG and permits the use of a smaller individual dose of MGBG and a shorter course of treatment than would be required with the use of MGBG alone.

Suitable dosages of the compounds of Formula I for use in combination therapy with MGBG or other cancer chemotherapeutic agents can be any amount effective in inhibiting polyamine biosynthesis sufficiently to control the tumor growth rate or to achieve a heightened response to the cytotoxic agent administered in conjunction therewith.

The term "controlling the growth of pathogenic parasitic protozoa", as used herein, means slowing, interrupting, arresting, or stopping the replication of the protozoa in an infected host. The compounds of Formula I are useful against *T.b. brucei* (which causes trypanosomiasis in cattle), *T.b. rhodesiense*, (which causes human sleeping sickness), the coccidia, for example, *Eimeria tenella* (which causes intestinal coccidiosis in fowl (e.g. chickens, turkeys, and ducks)) and the exo-erythrocytic form of plasmodia, for example, *plasmodium falciparum* (which causes human malaria).

The antiprotozoal activity of the compounds of Formula I can be demonstrated in vivo or in vitro in standard microbiological test procedures. For example, the activity of the compounds against *T.b. brucei*, and *T.b rhodesiense* can be determined in infected mice by administering the test compound ad lib daily (3 to 15 days post infection) as a solution in the drinking water. Activity is indicated by an increase in survival time (as compared to untreated controls) or by the absence of parasites in the blood. The activity of the compounds against the coccidia can be determined in infected chickens, for example those infected with *E. tenella* by administering the test compound daily ad lib (from one day pre injection to five days post infection) as a solution in the drinking water. The cecal lesions are evaluated by a standard lesion scoring procedure. (See Reid. *Am. J. Vet Res.*, 30, 447 (1969) and *Avian Coccidiosis*, P. Long. Editor, British Poultry Science, Ltd., Edinburgh). The activity of the compounds against malaria (*p.faleiparum*) can be determined by a standard in vitro plate culture test (See K. Rieckmann et al, *Lancet*, 1, 22 (1978)). Antimalarial activity can also be determined in special strains of mice infected with the exo-erythrocitic form of *p.berghei*. In this test, the compound is administered ad lib in drinking water starting two days pre-infection and continuing 28 days post-infection. Activity is measured by a significant decrease in deaths as compared to controls or by a significant increase in survival time.

The compounds of this invention can be administered in various manners to achieve the desired effect. The compounds can be administered alone or in the form of pharmaceutical preparations either orally or parenterally, for example, subcutaneously, intravenously or interperitoneally. The amount of novel compound administered will vary and can be any effective amount. Depending upon the patient, the condition being treated and the mode of administration, the effective dosage of the compound administered may vary from about 5 mg/kg to about 500 mg/kg, of body weight of the patient per day. Unit doses of these compounds can contain, for example, from about 10 mg to 500 mg of the compounds and may be administered, for example, from 1 to 4 times daily.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In the composition aspect of the invention there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. For making these formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable carriers or diluents are well known per se.

The formulations of the invention may be adapted for enteral or parenteral use and may be administered to the patient in the form of tablets, capsules, suppositories, solutions, suspensions or the like.

In the specific examples included hereinbelow illustrative examples of suitable pharmaceutical formulations are described.

Methods of preparing the compounds of Formula I will now be described. If in any of the reaction steps described an amino group of a reactant would be involved in an unwanted reaction under the relevant reaction conditions, the amino group will be protected in manner known per se by introduction of an appropriate protecting group. The protecting group will be chosen having regard to the nature of the relevant reaction and ease of removal to free the amino group. The protecting group can be selected from, for example, acyl, for example, lower alkanoyl, e.g. acetyl, propionyl, trifluoroacetyl, and the like; aroyl, e.g. benzoyl, toluoyl and the like; lower alkoxycarbonyl, for example methoxycarbonyl, ethoxycarbonyl, tert-butoxycarbonyl and the like; carbobenzoxy, benzenesulfonyl and tosyl. Both amino hydrogen atoms can be substituted by a single protecting group such as, for example phthalyl. The protecting groups are introduced in manner known per se by, for example, reaction of the amine with a lower alkanoyl or aroyl chloride, anhydride, sulfonylchloride, tert-butoxycarbonyloxyimino-2-phenylacetonitrile (BOC-ON), or di-tertbutyl dicarbonate ((BOC)₂O).

Removal of the protecting group after the required reaction has been completed can be carried out in manner known per se for the relevant protecting group. Usually, said removal will be by hydrolytic cleavage using a strong organic or mineral acid such as, for example, trifluoroacetic acid, hydrochloric acid and the like acids; or by hydrogen chloride gas under anhydrous conditions. The use of conditions which will reduce the unsaturated bond or of reactants, such as hydrobromic acid, which will react with the unsaturated bond must be avoided. Solvents used will be chosen dependent upon the conditions of protecting group removal. For example, ethers such as, for example, diethylether can be used for cleavage using hydrogen chloride gas.

In the case where an acetylenic group is to be protected, the preferred protecting group is trialkylsilyl, especially trimethylsilyl, which readily can be introduced by reaction of the free acetylenic group with a trialkylsilyl chloride. The trialkylsilyl group readily can be removed by base hydrolysis to free the acetylenic group.

Compounds of Formula I can be prepared from the corresponding alcohol of the following general Formula II by conversion in manner known per se of the hydroxyl group into a primary amino group:

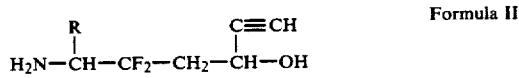

Formula II wherein R represents hydrogen or $C_1$–$C_4$ alkyl.

Preferably, the conversion of the hydroxy group proceeds via an amino-protected derivative of the corresponding phthalimido compound of the following general Formula III:

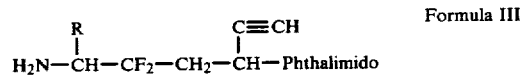

Formula III

The phthalimido compound of Formula III can be obtained in manner known per se by treating an amino-protected derivative of the compound of Formula II with phthalimide in the presence of a trialkyl- or triarylphosphine and diethylazodicarboxylate in an anhydrous aprotic solvent. Usually 1 to 3 equivalents each of phthalimide, the phosphine and diethylazodicarboxylate will be used per equivalent of Formula II derivative at a temperature of 10° C. to 100° C. for a period of 18 to 24 hours. Conveniently, the phosphine is triphenylphosphine and the aprotic solvent is tetrahydrofuran.

The phthalimido group can be converted in manner known per se into the required primary amino group. For example, the phthalimido group can be hydrolytically cleaved by heating with a strong mineral acid, preferably a mixture of hydrochloric and acetic acids. Acids which are reactive towards acetylenic bonds, e.g. hydrobromic acid, obviously cannot be used. It is preferred to free the amino group by heating, preferably under reflux conditions, the phthalimido derivative with a hydrazine or methylamine in a polar organic solvent, especially an alcohol. Conveniently, methylhydrazine in methanol is used.

The preferred amino-protecting group for the compound of Formula III is phthalimido, whereby both amino groups of the desired compound of Formula I can be freed simultaneously.

The compounds of Formula II can be obtained by reaction in manner known per se of an ethynyl magnesium halide, preferably the bromide, with an amino-protected derivative of the corresponding aldehyde of the following general Formula IV:

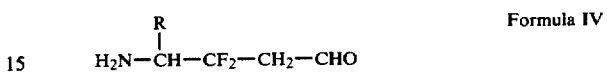

Formula IV wherein R represents hydrogen or $C_1$–$C_4$ alkyl.

Conveniently, the reaction is carried out in tetrahydrofuran and the ethynyl magnesium halide is formed in situ by adding ethyl magnesium halide to tetrahydrofuran saturated with acetylene. Again, the preferred amino protecting group is phthalimido.

The compounds of Formula IV can be obtained in manner known per se by oxidation of an amino-protected derivative of the corresponding olefin of the following general Formula V:

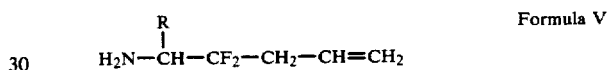

Formula V wherein R represents hydrogen or $C_1$–$C_4$ alkyl. Suitable oxidizing agents include potassium permanganate, osmium tetroxide and, presently preferred, ozone. When using ozone, it is preferred to pass the ozone through a solution of the olefin in a non-protic solvent, for example dichloromethane, and subsequently to add dimethylsulfide to reduce the ozonide reaction intermediate.

The compounds of Formula V can be obtained from the corresponding alcohol of the following general Formula VI by conversion in manner known per se of the hydroxyl group to primary amino group:

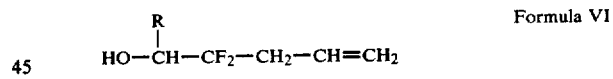

Formula VI wherein R represents hydrogen or $C_1$–$C_4$ alkyl. Conveniently, the conversion proceeds via the corresponding tosyloxy, mesyloxy or, preferably, trifluoromethylsulfonyloxy compound by treating the alcohol of Formula VI with tosyl chloride, mesyl chloride or trifluoromethylsulfonyl anhydride in the presence of a base such as pyridine in a non-protic solvent, especially dichloromethane. The intermediate is then treated with an alkali metal phthalimide in a polar organic solvent, suitably dimethylformamide, to form the corresponding phthalimido derivative. Usually, the phthalimido derivative will be used as the amino-protected derivative required as a reactant for the preparation of a compound of Formula V. However, if required, the amino group can be freed by, for example, treatment with a mineral acid or hydrazine.

The alcohol of Formula VI in which R represents hydrogen, can be obtained by reduction of the corresponding ester of the following general Formula VII with a reducing agent, such as a borohydride, which selectively reduces the ester group $R_1O_2C-CF_2-CH_2-CH=CH_2$ Formula VII wherein $R_1$ represents $C_1$-$C_4$ alkyl.

When R represents alkyl, the alcohol of Formula VI can be obtained by treating an ester of Formula VII with the corresponding lithium or magnesium alkyl halide to give the corresponding ketone of the following general Formula VIII

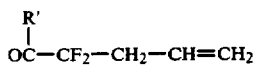
$OC-CF_2-CH_2-CH=CH_2$

Formula VIII wherein R' represents $C_1$-$C_4$ alkyl. The ketone of Formula VIII is then reduced to the desired alcohol with, for example, a borohydride.

The compounds produced by the foregoing processes may be isolated either per se or as acid addition salts thereof.

The acid addition salts are preferably the pharmaceutically acceptable, non-toxic addition salts with suitable acids such as those previously referred to in this Specification. Apart from pharmaceutically acceptable acid addition salts, other salts are also included within the scope of acid addition salts, such as for example, those with picric or oxalic acid; they may serve as intermediates in the purification of the compounds or in the preparation of other, for example, pharmaceutically acceptable, acid addition salts, or are useful for identification or characterisation of the bases.

A resulting acid addition salt may be converted into the free compound according to known methods, for example, by treating it with an alkali or alkaline earth metal hydroxide or alkoxide; with an alkali metal or an alkaline earth metal carbonate or hydrogen carbonate; with trialkylamine; or with an anion exchange resin.

A resulting acid addition salt may also be converted into another acid addition salt according to known methods; for example, a salt with an inorganic acid may be treated with a sodium, barium or silver salt of an acid in a suitable diluent, in which a resulting inorganic salt is insoluble and is thus removed from the reaction medium. An acid addition salt may also be converted into another acid addition salt by treatment with an anion exchange preparation.

The invention is illustrated by the following non-limiting Examples.

EXAMPLE
1,4-DIAMINO-2,2-DIFLUORO-HEX-5-YNE (FORMULA I; R=H)

(A) 2,2-DIFLUOROPENT-4-EN-1-OL (FORMULA VI; R=H)

A solution of ethyl 2,2-difluoropent-4-enoate Formula VII; $R_1=C_2H_5$) (146.8 g, 0.9 mol) in ethanol (350 mL) is added dropwise over a period of 1 hour to a solution of sodium borohydride (34 g, 0.9 mol) in absolute ethanol (550 mL) at room temperature. During the addition, the reaction mixture is observed to warm. After 25 min. the mixture is cooled with salt/ice to about 16° C. and the addition is continued at this temperature. Stirring is continued for a further 30 min. at ice-bath temperature and then for 2 hours at room temperature.

The reaction mixture is evaporated, the residue dissolved in dichloromethane (500 mL) and 4N sulfuric acid (350 mL) is added causing vigorous evolution of hydrogen. The solution is diluted with water (500 mL) and then extracted with dichloromethane (4×250 mL). The combined organic extracts are washed with sulfuric acid (twice, 200 mL, 2N), brine, dried over magnesium sulfate and concentrated at 25° C. under water-pump aspiration.

Distillation of the concentrate gives 2,2-difluoropent-4-en-1-ol b.p. 48-50 ° C./11 mm Hg as a colourless mobile oil (110.8 g, quantitative).

$^1$H NMR CDCl$_3$ delta 6.1-5.7 (1 H, m); 5.3 (2 H, br.d); 3.70 (2 H, t, J=12 Hz); 3.2 (1 H, br.s); 2.70 (2 H, dt, J=6, 15 Hz).

$^{19}$FNMR CDCl$_3$/C$_6$F$_6$—54 (tt, J=12.15 Hz).

(B) 2,2-DIFLUOROPENT-4-ENYL TRIFLUOROMETHYLSULFONATE

To a solution of the alcohol prepared in Step A above (78 g, 0.64 mol) in dichloromethane (500 mL) and pyridine (55.3 g, 0.7 mol) at 0° C. is added a solution of trifluoromethylsulfonyl anhydride (204 g, 0.7 mol) in dichloromethane over 0.75 hour whilst maintaining the temperature at 5° C. with salt/ice cooling. After complete addition, the reaction mixture is allowed to warm to room temperature, stirred for 0.5 hour, cooled to 0° C., and water (350 mL) then added. The resultant layers are separated, the aqueous layer extracted with dichloromethane (2×500 mL), the combined organic phase back washed with water (2×200 mL), dried over sodium sulfate and concentrated by rotary evaporation.

The concentrate is distilled at water pump pressure: b.p. 50°-52° C. 134 g (83%), $^1$H NMR CDCl$_3$ delta 5.8 (1 H, m); 5.3 (2 H, m); 4.50 (2 H, t, J=11 Hz); 2.77 (2 H, dt, J=7, 16 Hz)

$^{19}$F NMR CDCl$_3$/C$_6$F$_6$—88 (s), —57 (tt, J=11, 16 Hz).

(C) 2,2-DIFLUOROPENT-4-ENYL PHTHALIMIDE (FORMULA V; R=H; phthalyl protecting group)

Potassium phthalimide (123 g, 0.67 mol) is added to a stirred solution of 2,2-difluoropent-4-enyl trifluoromethylsulphonate prepared in Step B above (130 g, 0.51 mol) in dimethylformamide (1.2 L). The mixture is heated at 120° C. for 21 hours during which time most of the solid dissolves.

After cooling to room temperature, water (2 L) is added whilst maintaining the temperature at 20° C. The solid is dissolved by addition of diethylether, the ether layer separated, the aqueous layer extracted with diethylether (3×1.7 L). The combined organic layers are washed with 2N sodium hydroxide (3×150 mL), water (3×500 mL), dried (MgSO$_4$) and evaporated to yield 2,2-difluoropent-4-enyl phthalimide; (114.8 g, 90%) as a white solid; m.p. 74°-77°- C.

$^1$H NMR CDCl$_3$ delta 7.87 (4 H, m); 5.9 (1 H, m); 5.3 (2 H, m); 4.10 (2 H t, J=14 Hz); 2.75 (2 H, dt, J=7, 16 Hz).

$^{19}$F NMR CDCl$_3$/C$_6$F$_6$—60.5 (tt, J=16, 14 Hz).

A sample crystallised from diethylether/pentane has m.p. 78°-80° C.

Found: C, 62.53; H, 4.51; N, 5.63% C$_{13}$H$_{11}$NO$_2$F$_2$ requires: C, 62.15; H, 4.41; N, 5.58%

(D) 2,2-DIFLUORO-1-PHTHALIMIDOBUTAN-4-AL (FORMULA IV; R=H; phthalyl protecting group)

A solution of 2,2-difluoropent-4-enyl phthalimide prepared in Step C (18 g, 72 mmol) in dichloromethane (500 mL) is cooled in a dry-ice/acetone bath, and ozone (0.5 mmol/min) is bubbled into the solution until a blue coloration is observed. The ozone stream is stopped and dimethyl sulfide (60 mL) is added in one portion. The cooling bath is removed and the mixture stirred at room temperature overnight. Dichloromethane and excess dimethyl sulfide are removed by rotary evaporation. The residue is taken up in dichloromethane (100 mL), washed with saturated aqueous sodium bicarbonate (3×40 mL), twice with water (50 mL), then with brine, dried over sodium sulfate, and the solvent is removed by rotary evaporation, to give 2,2-difluoro-1-phthalimidobutan-4-al (18.1 g, 100%) as a white solid (m.p. 76°-78° C.).

$^1$H NMR CDCl$_3$ delta 9.87 (1 H, m); 7.87 (4 H, m); 4.22 (2 H, t, J=14 Hz); 3.07 (2 H, dt, J=2, 17 Hz).

$^{19}$F NMR CDCl$_3$/C$_6$F$_6$-64 (ddd, J=17, 14, 2 Hz)

If the reaction is left only 1 to 2 hours after addition of the dimethyl sulfide then the ozonide 3-(2,2-difluoro-3-phthalimidopropyl)-1,2,4-trioxalane is a major contaminant of the aldehyde:

$^1$H NMR CDCl$_3$ delta 7.53 (4 H, m); 5.60 (1 H, t, J=5 Hz); 5.22 (1 H, s); 5.13 (1 H, s); 4.17 (2 H, t, J=14 Hz); 2.45 (2 H, dt, J=5, 16 Hz).

$^{19}$F NMR CDCl$_3$/C$_6$F$_6$-62 (m).

(E)
2,2-DIFLUORO-1-PHTHALIMIDO-HEX-5-YN-4-OL (FORMULA II; R=H; phthalyl protecting group)

Dry ice-cold tetrahydrofuran (1 L) is saturated with acetylene over 1 hour. Ethyl magnesium bromide (2M solution in diethylether, 40 mL, 80 mmol) is then added to this solution over about 15 min, and, after the addition is complete, the acetylene stream is maintained for 30 min. A solution of the 2,2-difluoro-1-phthalimidobutan-4-al prepared in Step D (72 mmol) in tetrahydrofuran (150 mL) is then added dropwise over 15 min, and the mixture is stirred under nitrogen for 1 hour while being allowed to warm to room temperature.

The mixture is poured into 1N hydrochloric acid (1 L) and extracted with diethylether (3×750 mL). The combined organic extracts are washed with brine, dried over sodium sulfate and concentrated.

The product is treated with activated carbon in methanol. Crystallisation of this material from ethylacetate/hexane and chromatography of the mother liquors (500 g SiO$_2$ 70–230 mesh: ethylacetate/hexane 1:1) gives, in total, 6.58 g of 2,2-difluoro-1-phthalimido-hex-5-yn-4-ol of a purity adequate for use in Step F. Overall yield 33%, R$_f$(ethylacetate/hexane 1:1) 0.69. A sample recystallised from methanol has m.p. 172°-4° ° C.

$^1$H NMR (CD$_3$OD/(CD$_3$)$_2$SO) delta 7.87 (4 H, m); 4.67 (1 H, td, J=6, 2 Hz); 4.5-3.7 (2 H, m); 3.03 (1 H, d, J=2 Hz); 2.40 (2 H, ddd, j=18, 15 6 Hz).

$^{19}$F NMR CDCl$_3$/C$_6$F$_6$ -64 (m).

m.s. (NH$_3$/DCI) m/e 297 (MNH$_4$+, 70%); 280 (MH+, 100%); 262 (20%); 242 (50%); 160 (75%).

Found: C, 59.55; H, 4.06; N, 5.13% C$_{14}$H$_{11}$NO$_3$F$_2$ requires: C, 60.22; H, 3.97; N, 5.02%.

(F)
2,2-DIFLUORO-1,4-BIS(PHTHALIMIDO)-HEX-5-YNE (FORMULA III; R=H; phthalyl protecting group)

Diethyl azodicarboxylate (7.5 mL, 47.4 mmol) is added to an ice-cold solution of 2,2-difluoro-1-phthalimido-hex-5-yn-4-ol prepared in Step E (8.88 g, 31.8 mmol), triphenylphosphine (16.7 g, 63.7 mmol), and phthalimide (5.12 g, 34.8 mmol) in tetrahydrofuran (500 mL) under nitrogen over a period of 10 minutes. The mixture is stirred at 0° C. for 2 hours and then at room temperature for 65 hours.

The tetrahydrofuran is removed by rotary evaporation, and the residue purified by flash chromatography (800 g, SiO$_2$, 230–400 mesh; ethylacetate/hexane 1:1). Two sets of fractions are collected. Those containing 2,2-difluoro-4-bis-(phthalimido)-hex-5-yne and triphenylphosphine are washed with diethylether to give the desired bis-phthalimide of reasonable purity, while the fractions containing 2,2-difluoro-1,4-bis(phthalimido)-hex-5-yne and N,N'-dicarbethoxyhydrazine are washed with methanol. Finally, the column is washed with ethylacetate. Again methanol washing gives the bis-phthalimide. In total 4.85 g, 36% of the desired product are isolated; R$_f$(ethylacetate/hexane, 1:1) 0.34.

A sample washed once more with methanol has m.p. 201°-203° C.

$^1$H NMR (CDCl$_3$) delta 7.77 (8 H, m); 5.60 (1 H, ddd, J=9, 4, 2 Hz); 4.08 (2 H, t, J=14 Hz); 3.5-2.5 (2 H, m); 2.43 (1 H, d, J=2 Hz).

$^{19}$F NMR CDCl$_3$/C$_6$F$_6$-59 (m).

m.s (EI) m/e 408 (M+, 5%); 388 (m-HF, 15%); 380 (5%) 368 (10%); 345 (20%); 241 (95%); 184 (100%); 160 (80%).

Found: C, 63.86; H, 3.51; N, 6.83% C$_{22}$H$_{14}$N$_2$F$_2$O$_4$ requires: C, 64.71; H, 3.46; N, 6.86%

(G)
2,2-DIFLUOROHEX-5-YNE-1,4-DIAMINE-BIS-t-BUTYLCARBAMATE (FORMULA I; R=H; BOC protecting group)

Methylhydrazine (2.46 mL, 46 mmol) is added to 2,2-difluoro-1,4-bis(phthalimido)-hex-5-yne prepared in Step F (4.85 g, 11.9 mmol) in methanol (50 mL) and tetrahydrofuran (50 mL) and the solution is heated at 80° C. (gentle reflux) under nitrogen for 22 hours. The mixture is then cooled to room temperature and concentrated by rotary evaporation, finally with ethanol azeotrope.

The residue is suspended in a mixture of methanol (200 mL), water (10 mL), and conc. hydrochloric acid (20 mL) and stirred for 30 min. The solids are removed by filtration and washed with water. The combined filtrates are evaporated to dryness.

The residue is dissolved in water (25 mL) and tetrahydrofuran (25 mL). Sodium carbonate (5 g) and di-tert-butyldicarbonate (10 g, 45.9 mmol) are added and the mixture is stirred at room temperature overnight.

The mixture is extracted with diethylether (3×50 mL). The combined extracts are washed in brine, dried over sodium sulfate and evaporated. The residue is flash chromatographed (about 200 g SiO$_2$, 230–400 mesh, pentane/diethylether 2:1) to give 2,2-difluoro-hex-5-yne-1,4-diamine-bis-t-butylcarbamate 2.2 g, 53% R$_f$ 0.31.

A sample crystallised from pentane has m.p. 108°-115° C.

$^1$H NMR (CDCl$_3$) delta 4.8 (3 H, m); 3.57 (2 H, dt, J=6, 14 Hz); 2.3 (3 H, m); 1.47 (18 H, s).

$^{19}$F NMR CDCl$_3$/C$_6$F$_6$ -59.

(H) 2,2-DIFLUOROHEX-5-YNE-1,4-DIAMINE DIHYDROCHLORIDE (FORMULA I; R=H; dihydrochloride acid addition salt)

A saturated solution of hydrochloric acid in diethylether (20 mL) is added to a solution of 2,2-difluorohex-5-yne-1,4-diamino-bis-t-butylcarbamate prepared in Step G (2.2 g, 6.3 mmol) in diethylether (10 mL). The mixture is stirred at room temperature for 4 days. The precipitate is collected, washed with diethylether and recrystallised from methanol/di-isopropylether to give 2,2-difluorohex-5-yne-1,4-diamine dihydrochloride as a white, non-hygroscopic solid 1.09 g, 78%, which melts with decomposition above 200° C.

$^1$H NMR (D$_2$O: HDO=4.50 delta) delta 3.50 (2 H, dd, J=15, 18 Hz); 3.00 (1 H, d, J=2 Hz), 2.7 (2 H, m). The signal for H-4 is obscured by the solvent.

Found: C, 32.41/32.55; H, 5.31/5.36; N, 12.60/12.78%. C$_6$H$_{12}$N$_2$F$_2$Cl$_2$ requires: C, 32.60; H, 5.47; N, 12.67%.

In the following Examples relating to pharmaceutical compositions, the term "active compound" is used to indicate the compound 1,4-diamino-2,2-difluoro-hex-5-yne. This compound may be replaced in these compositions by any other compound of the invention, for example by 2,5-diamino-3,3-difluorohept-6-yne. Adjustments in the amount of medicament may be necessary or desirable depending upon the degree of activity of the medicament as is well known in the art

EXAMPLE 2

An illustrative composition for hard gelatin capsules is as follows:

| (a) active compound | 20 mg |
| (b) talc | 5 mg |
| (c) lactose | 90 mg |

The formulation is prepared by passing the dry powders through a fine mesh screen and mixing them well. The powder is then filled into hard gelatine capsules at a net fill of 115 mg per capsule.

EXAMPLE 3

An illustrative composition for tablets is as follows:

| (a) active compound | 20 mg |
| (b) starch | 43 mg |
| (c) lactose | 45 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 4

An illustrative composition for an injectable suspension is the following 1 ml ampule for an intramuscular injection:-

| | weight percent |
|---|---|
| (a) active compound | 1.0 |
| (b) polyvinylpyrrolidone | 0.5 |
| (c) lecithin | 0.25 |
| (d) water for injection to make | 100.0 |

The materials are mixed, homogenized, and filled into 1 ml ampuls which are sealed and autoclaved for 20 minutes at 121° C. Each ampule contains 10 mg per ml of novel compound (a).

EXAMpLE 5

| | mg/suppository |
|---|---|
| Active Compound | 50 |
| Oil of Theobroma | 950 |

The medicament is powdered and passed through a B.S. No. 100 sieve and triturated with molten oil of theobroma at 45° C. to form a smooth suspension. The mixture is well stirred and poured into moulds each of nominal 1 G capacity, to produce suppositories.

EXAMPLE 6

The ODC inhibitory activity of the compounds of Formula I can be demonstrated in vivo according to the following procedure:

Male rats of the Sprague-Dawley strain (200–220 g body weight) are given food and water ad libitum under a constant 12 hr light- 12 hr dark lighting schedule. Drugs are injected intraperitoneally (dissolved in 0.9% saline) or are given by gavage (dissolved in water). Rats given saline or water serve as control. Five to six hours after drug administration, the animals are killed by decapitation and the ventral prostate and thymus are excised rapidly and immediately processed. The tissues are homogenized with three volumes of 30 mM sodium phosphate buffer (pH 7.1) containing 0.1 mM EDTA, 0.25M sucrose, 0.1 mM pyridoxal phosphate and 5 mM dithiothreitol. Ornithine decarboxylase activities are determined on a 1000 g supernatant of prostate homogenate and on a whole thymus homogenate, essentially as described by Ono et al (Biochem. Biophys. Acta, 284, 285 (1972)).

EXAMPLE 7

The activity of the compounds of Formula I as inhibitors of ornithine decarboxylase (ODC) can be demonstrated in vitro according to the following procedure:

Ornithine decarboxylase (ODC) is prepared from the livers of rats which have been injected with thioacetamide (150 mg/kg of body weight) 18 hrs before sacrifice, and is purified about ten fold by acid treatment at pH 4.6 as described by Ono et al (Biochem. Biophys. Acta 284, 285 (1972)). The stock solution of ODC is comprised of protein (16 mg/mL), sodium phosphate buffer (30 mM, pH 7.1), dithiothreitol (5 mM) and pyridoxal phosphate (0.1 mM). The specific activity of this stock solution is 0.12 nmol of CO$_2$/min per mg of protein. For a typical experiment 320 l of this stock solution are mixed at time 0 with 80 l of a solution of the inhibitor in water and incubated at 37°. At different times 50 l aliquots are transferred into a 1-mL assay medium containing sodium phosphate (30 mM, pH 7.1), dithiothreitol (5 mM), pyridoxal phosphate (0.1 mM), L-ornithine (0.081 mol), and DL-[1-$^{14}$C] ornithine (0.043 mol, 58 Ci/mol, Amersham) in a closed vessel in which a filter paper moistered with 50 l hyamine hydroxide (1M) is fitted. The reaction is allowed to proceed for 60 min at 37° C. and then terminated by addition of 0.5 ml of 40% trichloroacetic acid. After an additional 30 min the CO$_2$ absorbed on the filter paper is counted in a standard scintillation cocktail. K$_I$ (apparent dissociation constant) and T50 (half-life, at infinite concentration of inhibitor are calculated according to the method of Kitz and Wilson (J. Biol. Chem., 237, 3245 (1962)).

We claim:

1. A fluorinated diaminoalkyne derivative of the formula

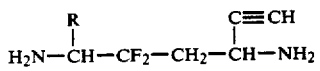

wherein R represents hydrogen or $C_1$–$C_4$ alkyl.

2. 1,4-Diamino-2,2-difluoro-5-yne or a pharmaceutically acceptable salt thereof.

3. A compound as claimed in claim 1 or claim 2, for use in a method of treatment of the human or animal body by therapy or of diagnosis practiced on the human or animal body.

4. A compound as claimed in claim 1 or claim 2, for use in the inhibition in the human or animal body of ornithine decarboxylase.

5. A pharmaceutical composition comprising a compound as claimed in claim 1 or claim 2 in admixture or otherwise in association with a pharmaceutically acceptable carrier or diluent therefor.

6. A pharmaceutical composition as claimed in claim 5 in unit dosage form containing 10 mg to 500 mg of said compound per unit dose.

7. The use of a compound as claimed in claim 1 or claim 2 for the manufacture of a medicament for the inhibition of ornithine decarboxylase in the human or animal body.

8. A method of inhibiting ornithine decarboxylase in a patient in need thereof which comprises administering to said patient an effective ornithine decarboxylase inhibiting amount of a compound as defined in claim 1.

9. A method of controlling the growth of tumor tissue in a patient having tumor tissue which comprises administering to said patient an effective tumor inhibiting amount of a compound as defined in claim 1.

10. A method as defined in claim 8 or claim 9 wherein the compound administered is 1,4-diamino-2,2-difluoro-hex-5-yne.

* * * * *

UNITED STATES PATENT AND TRADEMARK OFFICE
CERTIFICATE OF CORRECTION

PATENT NO. : 4,707,498

DATED : November 17, 1987

INVENTOR(S) : Michael Kolb, et al.

It is certified that error appears in the above-identified patent and that said Letters Patent are hereby corrected as shown below:

At column 3, line 37, and at column 4, line 34, the patent reads "malignent" and should read --malignant--.

At column 14, line 62, the patent reads "moistered" and should read --moistened--.

At column 15, line 11, claim 1, the patent reads "or $(C_1-C_4)$" and should read --or $(C_1-C_4)$alkyl, or a pharmaceutically acceptable salt thereof.--

Signed and Sealed this

Seventh Day of June, 1988

Attest:

DONALD J. QUIGG

Attesting Officer  Commissioner of Patents and Trademarks